(12) United States Patent
Fouque et al.

(10) Patent No.: US 6,596,880 B1
(45) Date of Patent: Jul. 22, 2003

(54) METHOD FOR PREPARING TAXANE DERIVATIVES

(75) Inventors: Elie Fouque, Saint Maur des Fosses (FR); Jean-Manuel Mas, Villeurbanne (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 08/256,736

(22) PCT Filed: Feb. 4, 1993

(86) PCT No.: PCT/FR93/00110
§ 371 (c)(1),
(2), (4) Date: Aug. 2, 1994

(87) PCT Pub. No.: WO93/16059
PCT Pub. Date: Aug. 19, 1993

(30) Foreign Application Priority Data

Feb. 7, 1992 (FR) .............................. 92 01379

(51) Int. Cl.$^7$ ............................. C07D 305/14
(52) U.S. Cl. ....................... 549/510; 549/511
(58) Field of Search ................. 549/510, 511

(56) References Cited

U.S. PATENT DOCUMENTS

| 4,924,011 A | 5/1990 | Denis et al. ................. 549/510 |
| 4,924,012 A | 5/1990 | Colin et al. ................. 549/510 |

FOREIGN PATENT DOCUMENTS

| FR | 0 336 840 | 10/1989 |
| FR | 0 336 841 | 10/1989 |

OTHER PUBLICATIONS

Swindell et al, J. Med. Chem., vol. 34, No. 3, pp. 1176–1184., 1991.*
V. Senilh et coll., C.R. Acad. Sci. Paris, t.299, serie II, n° 15, 1039 (1984).
F. Guéritte–Voegelein et al., Tetrahedron, 42 (16), 4451–4460 (1986).
J–N. Denis et coll., J. Amer. Chem. Soc., 110, 5917–5919 (1988).
L. Mangatal et al., Tetrahedron, 45 (13), 4177–4180 (1989).
F. Guéritte–Voeglein et al., J. Med. Chem., 34, 992–998 (1991).

* cited by examiner

Primary Examiner—Ba K. Trinh
(74) Attorney, Agent, or Firm—Finnegan, Henderson, Farabow, Garrett & Dunner LLP

(57) ABSTRACT

This invention relates to a method for preparing taxane derivatives of general formula (I)

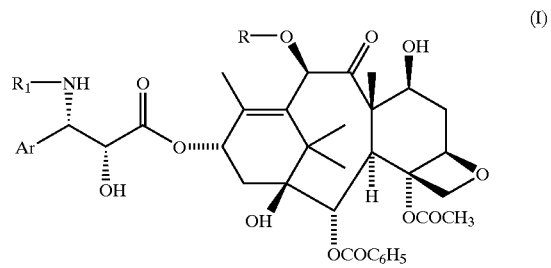

by esterification at a temperature between −10 and 60° C. of a derivative of baccatine III or 10-deacetyl baccatine III of general formula (II)

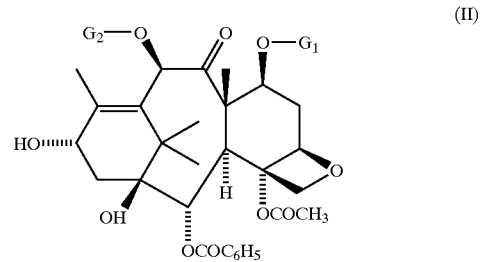

by means of an acid of general formula (III),

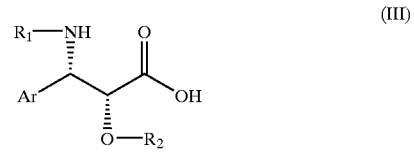

followed by replacement of the protective groupings $G_1$, $G_2$ and $R_2$ of the resulting product by hydrogen atoms. In formulae (I), (II) or (III), Ar stands for an aryl radical; R stands for hydrogen or acetyl; $R_1$ is benzoyl or ter.butoxycarbonyl; $G_1$ is a hydroxy function protective grouping, $G_2$ stands for the acetyl radical or a hydroxy function protective grouping, and $R_2$ stands for a hydroxy function protective grouping.

18 Claims, No Drawings

METHOD FOR PREPARING TAXANE DERIVATIVES

This application is a 371 of PCT/FR93/00110 dated Feb. 4, 1993.

FIELD OF THE INVENTION

The present invention relates to a new method for preparing taxane derivatives of general formula:

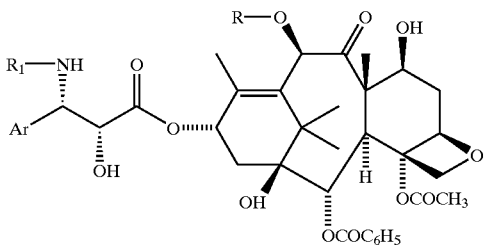

in which Ar represents an aryl radical, R represents a hydrogen atom or the acetyl radical and $R_1$ represents a benzoyl or tert-butoxycarbonyl radical, which derivatives display noteworthy antitumour properties.

BACKGROUND OF THE INVENTION

It is known, from American Patents U.S. Pat. No. 4,924,011 and U.S. Pat. No. 4,924,012, to prepare taxane derivatives of general formula (I) by esterification of a derivative of baccatine III or of 10-deacetyl baccatine III of general formula:

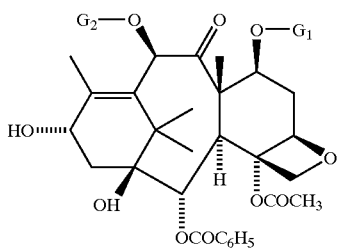

in which $G_1$ represents a protecting group for the hydroxyl function such as the 2,2,2-trichloroethoxycarbonyl radical or a replacement, by hydrogen atoms, of the protecting groups $G_1$, $G_2$ and $R_2$ of the product obtained.

The esterification is carried out in the presence of a condensing agent such as a carbodiimide, for instance dicyclohexylcarbodiimide, or a reactive carbonate, for instance 2-dipyridyl carbonate, and an activating agent such as a dialkylaminopyridine, for instance 4-dimethylaminopyridine, working in an organic aromatic solvent such as benzene, toluene, xylenes, ethylbenzene, isopropylbenzene or chlorobenzene at a temperature between 60 and 90° C.

Replacement of the protecting groups by hydrogen atoms is carried out using zinc in acetic acid or by hydrolysis in an acidic medium.

It has now been found, and this forms the subject of the present invention, that the esterification of the alcohol of general formula (II) using the acid of general formula (III) may be performed at a temperature between −10 and 60° C. (60° C. not inc), preferably between 20 and 35° C., working in an organic solvent chosen from ethers such as tetrahydrofuran, diisopropyl ether, methyl tert-butyl ether or dioxane, ketones such as methyl isobutyl ketone, nitriles such as acetonitrile, esters such as ethyl acetate, isopropyl acetate or n-butyl acetate, aliphatic hydrocarbons such as pentane, hexane or heptane, hydrogen atoms is carried out using zinc in acetic acid or by hydrolysis in an acidic medium.

DESCRIPTION OF THE INVENTION

It has now been found, and this forms the subject of the present invention, that the esterification of the alcohol of general formula (II) using the acid of general formula (III) may be performed at a temperature between −10 and 60° C., preferably between 20 and 35° C., working in an organic solvent chosen from ethers such as tetrahydrofuran, diisopropyl ether, methyl tert-butyl ether or dioxane, ketones such as methyl isobutyl ketone, nitriles such as acetonitrile, esters such as ethyl acetate, isopropyl acetate or n-butyl acetate, aliphatic hydrocarbons such as pentane, hexane or heptane, chlorinated aliphatic hydrocarbons such as dichloromethane or 1,2-dichloroethane and aromatic hydrocarbons such as benzene, toluene and xylenes. Esters and aromatic hydrocarbons are very particularly advantageous.

The esterification is generally carried out in the presence of a condensing agent such as a carbodiimide, for instance dicyclohexylcarbodiimide, and an activating agent such as an aminopyridine, for instance 4-dimethylaminopyridine or 4-pyrrolidinopyridine.

It is advantageous to perform the esterification using an excess of acid of general formula (III) relative to the alcohol of general formula (II), but the reaction may also be carried out using a stoichiometric amount of acid of general formula (III) and of alcohol of general formula (II). The condensing agent is generally used in a stoichiometric amount relative to the acid of general formula (III) and the activating agent represents a stoichiometric amount or less relative to the alcohol of general formula (II).

Since the method according to the invention is implemented at a temperature below that of the methods known previously, it allows higher yields of ester to be obtained due to the greater stability of the acid of general formula (III) in the reaction mixture and to the decrease in side reactions.

EXAMPLES

The examples which follow illustrate the present invention.

Example 1

1.0045 g of 96% 4-acetoxy-2α-benzoyloxy-5β,20-epoxy-1,13α-dihydroxy-9-oxo-7β,10β-bis(2,2,2-trichloroethoxy)carbonyloxy-11-taxene (equivalent to 1.08 mmol), 1.1545 g of 100% (2R,3S)-2-(1-ethoxyethoxy)-3-tert-butoxycarbonylamino-3-phenylpropionic acid (equivalent to 3.3 mmol), 0.6669 g of 99% dicyclohexylcarbodiimide (equivalent to 3.2 mmol), 0.0742 g of 98% 4-pyrrolidinopyridine (equivalent to 0.49 mmol) and 6 cm³ of anhydrous toluene are introduced into a 20 cm³ conical flask. The mixture is stirred vigorously for 72 hours while maintaining the temperature at −10° C.

Assay of the reaction medium by high performance liquid chromatography shows that the medium contains 1.1370 g of 4-acetoxy-2α-benzoyloxy-5β,20-epoxy-1-hydroxy-9-oxo-7β,10β-bis(2,2,2-trichloroethoxy)carbonyloxy-11-taxen-13α-yl (2R,3S)-3-tert-butoxycarbonylamino-3-phenyl-2-(1-ethoxyethoxy)-propionate (equivalent to 0.91 mmol) and 0.1705 g of 4-acetoxy-2α-benzoyloxy-5β,20-epoxy-1-hydroxy-9-oxo-7β,10β-bis(2,2,2-trichloroethoxy)carbonyloxy-11-taxen-13α-yl (2S,3S)-3-tert-butoxycarbonylamino-3-phenyl-2-(1-ethoxyethoxy)-propionate (equivalent to 0.14 mmol).

The overall yield is 97% with a degree of epimerization of 12.7%.

Example 2

50.011 g of 96% 4-acetoxy-2α-benzoyloxy-5β,20-epoxy-1,13α-dihydroxy-9-oxo-7β,10β-bis(2,2,2-trichloroethoxy)carbonyloxy-11-taxene (equivalent to 53.6 mmol), 56.81 g of 100% (2R,3S)-2-(1-ethoxyethoxy)-3-tert-butoxycarbonylamino-3-phenylpropionic acid (equivalent to 160.7 mmol), 33.54 g of 99% dicyclohexylcarbodiimide (equivalent to 160.9 mmol), 1.79 g of 98% 4-pyrrolidinopyridine (equivalent to 11.8 mmol) and 299 cm³ of anhydrous toluene are introduced into a 500 cm³ jacketed glass reactor fitted with a nitrogen inlet, a temperature probe and a condenser. The mixture is stirred vigorously for 12 hours while maintained at a temperature in the region of 25° C.

Assay of the reaction medium by high performance liquid chromatography shows that the medium contains 57.00 g of 4-acetoxy-2α-benzoyloxy-5β,20-epoxy-1-hydroxy-9-oxo-7β,10β-bis(2,2,2-trichloroethoxy)carbonyloxy-11-taxen-13α-yl (2R,3S)-3-tert-butoxycarbonylamino-3-phenyl-2-(1-ethoxyethoxy)-propionate (equivalent to 45.7 mmol) and 8.52 g of 4-acetoxy-2α-benzoyloxy-5β,20-epoxy-1-hydroxy-9-oxo-7β,10β-bis(2,2,2-trichloroethoxy)carbonyloxy-11-taxen-13α-yl (2S,3S)-3-tert-butoxycarbonylamino-3-phenyl-2-(1-ethoxyethoxy)-propionate (equivalent to 6.8 mmol).

The overall yield is 98% with a degree of epimerization of 13.0%.

Examples 3 to 19

250 mg of 96% 4-acetoxy-2α-benzoyloxy-5β,20-epoxy-1,13α-dihydroxy-9-oxo-7β,10β-bis(2,2,2-trichloroethoxy)carbonyloxy-11-taxene (equivalent to 0.27 mmol), 284 mg of 100% (2R,3S)-2-(1-ethoxyethoxy)-3-tert-butoxycarbonylamino-3-phenylpropionic acid (equivalent to 0.80 mmol), 190 mg of 99% dicyclohexylcarbodiimide (equivalent to 0.91 mmol), 9 mg of 98% 4-dimethylaminopyridine (equivalent to 0.07 mmol) and 3 cm³ of solvent are introduced into a 10 cm³ conical flask. The reaction medium is stirred vigorously while maintained at a temperature in the region of 30° C.

After stirring for 16 to 24 hours, assay of the reaction medium by high performance liquid chromatography allow the yield of esterification and the degree of epimerization to be calculated.

The results which are obtained with various solvents are collated in the following table.

| Example | Solvent | Duration of the reaction (hours) | Yield of esterification | Degree of epimerization (%) |
|---|---|---|---|---|
| 3 | Tetrahydrofuran | 17.0 | 24.5 | 7.3 |
| 4 | Diisopropyl ether | 23.5 | 87.4 | 14.2 |
| 5 | Methyl tert-butyl ether | 17.0 | 87.3 | 12.5 |
| 6 | Dioxane | 16.2 | 19.6 | 10.8 |
| 7 | Acetonitrile | 23.5 | 58.8 | 46.9 |

-continued

| Example | Solvent | Duration of the reaction (hours) | Yield of esterification | Degree of epimerization (%) |
|---|---|---|---|---|
| 8 | Benzene | 16.2 | 96.0 | 12.6 |
| 9 | Toluene | 23.5 | 98.0 | 13.9 |
| 10 | meta-Xylene | 17.0 | 97.8 | 14.4 |
| 11 | Anisole | 16.2 | 94.1 | 19.2 |
| 12 | Chlorobenzene | 16.2 | 96.0 | 17.5 |
| 13 | Cyclohexane | 17.0 | 61.7 | 15.8 |
| 14 | Pentane | 16.2 | 51.0 | 31.2 |
| 15 | n-Hexane | 23.5 | 42.1 | 29.7 |
| 16 | Heptane | 16.2 | 37.2 | 21.5 |
| 17 | 1,2-Dichloroethane | 17.0 | 92.8 | 28.9 |
| 18 | Dichloromethane | 17.0 | 83.7 | 26.6 |
| 19 | Methyl isobutyl ketone | 16.2 | 58.8 | 17.4 |
| 20 | Ethyl acetate | 8 | 75 | 12.7 |

Example 21

503.6 mg of 96% 4-acetoxy-2α-benzoyloxy-5β,20-epoxy-1,13α-dihydroxy-9-oxo-7β,10β-bis(2,2,2-trichloroethoxy)carbonyl-11-taxene (equivalent to 0.54 mmol), 579.0 mg of 99% (2R,3S)-2-(1-ethoxyethoxy)-3-tert-butoxycarbonylamino-3-phenylpropionic acid (equivalent to 1.62 mmol), 357.8 mg of 99% dicyclohexylcarbodiimide (equivalent to 1.72 mmol), 45.5 mg of 98% 4-pyrrolidinopyridine (equivalent to 0.30 mmol) and 3 cm³ of anhydrous toluene are loaded into a 10 cm³ conical flask. The mixture is stirred vigorously for 5 hours 20 minutes while maintaining the temperature at 45° C.

Assay of the reaction medium by high performance liquid chromatography shows that the medium contains 559.5 mg of 4-acetoxy-2α-benzoyloxy-5β,20-epoxy-1-hydroxy-9-oxo-7β,10β-bis(2,2,2-trichloroethoxy)carbonyloxy-11-taxen-13α-yl (2R,3S)-3-tert-butoxycarbonylamino-3-phenyl-2-(1-ethoxyethoxy)-propionate (equivalent to 0.45 mmol) and 90.8 mg of 4-acetoxy-2α-benzoyloxy-5β,20-epoxy-1-hydroxy-9-oxo-7β,10β-bis(2,2,2-trichloroethoxy)carbonyloxy-11-taxen-13α-yl (2S,3S)-3-tert-butoxycarbonylamino-3-phenyl-2-(1-ethoxyethoxy)-propionate (equivalent to 0.07 mmol).

The overall yield is 97% with a degree of epimerization of 13.9%.

What is claimed is:
1. Method for preparing a taxane derivative of the formula:

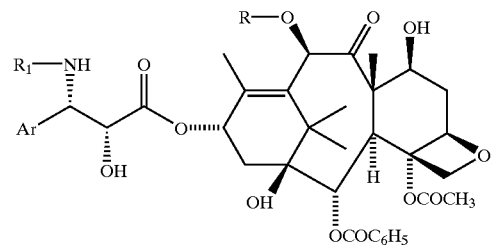

in which Ar represents an aryl radical, R represents a hydrogen atom or the acetyl radical and $R_1$ represents a benzoyl or tert-butoxycarbonyl radical, comprising esterification of a derivative of baccatine III or of 10-deacetyl baccatine III of the formula:

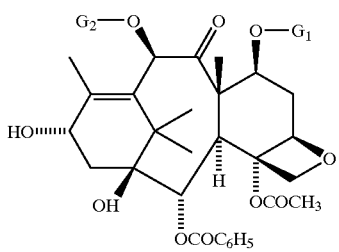

in which $G_1$ represents a protecting group for the hydroxyl function and $G_2$ represents the acetyl radical or a protecting group for the hydroxyl function, using an acid of the formula:

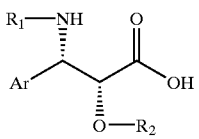

in which Ar and $R_1$ are defined as above and $R_2$ represents a protecting group for the hydroxyl function, followed by replacement, by hydrogen atoms, of the protecting groups $G_1$, $G_2$ and $R_2$ of the product obtained, and wherein the esterification is carried out at a temperature ranging from −10 to less than 60° C.

2. Method according to claim 1, wherein the esterification is carried out in an organic solvent selected from ethers, ketones, esters, nitriles, aliphatic hydrocarbons, chlorinated aliphatic hydrocarbons and aromatic hydrocarbons.

3. Method according to claim 2, wherein the solvent is selected from esters and aromatic hydrocarbons.

4. Method according to claim 1, wherein the esterification is performed in the presence of a condensing agent and an activating agent.

5. Method according to claim 4, wherein the condensing agent is a carbodiimide.

6. Method according to claim 4, wherein the activating agent is an aminopyridine.

7. Method according to claim 5, wherein the carbodiimide is dicyclohexylcarbodiimide.

8. Method according to claim 6, wherein the aminopyridine is 4-dimethylaminopyridine or 4-pyrrolidinopryidine.

9. Method according to claim 1, wherein $G_1$ represents a 2,2,2-trichloroethoxycarbonyl radical or a trialkylsilyl radical in which each alkyl part contains 1 to 4 carbon atoms, said protecting group for the hydroxyl function in $G_2$ represents the 2,2,2-trichloroethoxycarbonyl radical, and $R_2$ represents a methoxymethyl, 1-ethoxyethyl, benzyloxymethyl, (β-trimethylsilylethoxy)methyl, tetrahydropyranyl, 2,2,2-trichloroethoxymethyl or 2,2,2-trichloroethoxycarbonyl radical.

10. Method according to claim 1, wherein the esterification is carried out at a temperature ranging from −10° to 45° C.

11. Method according to claim 1, wherein the esterification is carried out at a temperature ranging from 20° to 45° C.

12. Method according to claim 1, wherein the esterification is carried out at a temperature ranging from 20° to 35° C.

13. Method according to claim 1, wherein the esterification is carried out at a temperature ranging from 25° to 30° C.

14. Method according to claim 1, wherein the molar ratio of said acid of the formula:

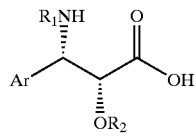

to said derivative of baccatine III or of 10-deacetyl baccatine III of the formula:

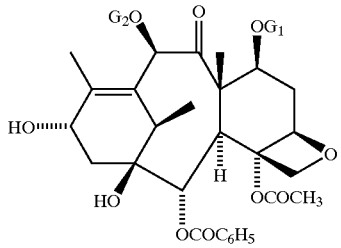

is about 3:1.

15. Method according to claim 1, wherein the esterification is carried out in an organic solvent selected from anhydrous toluene, diisopropyl ether, methyl tert-butyl ether, benzene, and meta-Xylene.

16. Method according to claim 1, wherein the esterification is carried out for a time not exceeding 72 hours.

17. Method according to claim 1, wherein the esterification is carried out for a time ranging from 5 hours to 24 hours.

18. Method according to claim 1, wherein the esterification is carried out for a time ranging from 12 hours to 24 hours.

* * * * *